United States Patent [19]

Ruddy et al.

[11] Patent Number: 5,718,919
[45] Date of Patent: Feb. 17, 1998

[54] NANOPARTICLES CONTAINING THE R(-) ENANTIOMER OF IBUPROFEN

[75] Inventors: Stephen B. Ruddy, Schwenksville; Mary E. Roberts, Downingtown, both of Pa.

[73] Assignee: NanoSystems L.L.C., Collegeville, Pa.

[21] Appl. No.: 393,648

[22] Filed: Feb. 24, 1995

[51] Int. Cl.$^6$ ........................................ A61K 9/16
[52] U.S. Cl. .................. 424/489; 424/470; 424/490; 424/488
[58] Field of Search ...................... 424/489, 490, 424/472, 488; 562/496; 514/570; 548/339

[56] References Cited

U.S. PATENT DOCUMENTS

| | | | |
|---|---|---|---|
| 4,915,953 | 4/1990 | Jordan et al. | 424/473 |
| 4,980,375 | 12/1990 | Sunshine et al. | 514/570 |
| 5,200,558 | 4/1993 | Kwan | 562/496 |
| 5,283,065 | 2/1994 | Doyon et al. | 424/489 |
| 5,399,707 | 3/1995 | Bhattacharya et al. | 548/339.1 |

*Primary Examiner*—Thurman K. Page
*Assistant Examiner*—William E. Benston, Jr.
*Attorney, Agent, or Firm*—Rudman & Balogh

[57] ABSTRACT

There is described a composition comprised of nanoparticles of a therapeutic agent having a surface modifier adsorbed on the surface thereof. The present composition is characterized in that the therapeutic agent is ibuprofen or fenoprofen which is substantially enriched in the R(-) enantiomer.

3 Claims, 4 Drawing Sheets

NANOPARTICLES CONTAINING THE R(−) ENANTIOMER OF IBUPROFEN

FIELD OF THE INVENTION

The present invention is directed to nanoparticles including the R(−) enantiomer of ibuprofen or fenoprofen as the therapeutic agent.

Background of Invention

Bioavailability is the degree to which a therapeutic agent becomes available to the target tissue after administration. Many factors can affect bioavailability including the dosage form and various properties, e.g., dissolution rate of the therapeutic agent. Poor bioavailability is a significant problem encountered in the development of pharmaceutical compositions, particularly those containing an active ingredient that is poorly soluble in water. Poorly water soluble therapeutic agents, i.e., those having a solubility less than about 10 mg/ml, tend to be eliminated from the gastrointestinal tract before being absorbed into the circulation.

Nanoparticles, described in U.S. Pat. No. 5,145,684, are particles consisting of a poorly soluble therapeutic onto which are adsorbed a non-crosslinked surface modifier, and which have an average particle size of less than about 400 nanometers (nm). These nanoparticles provide for increased bioavailability and for improved diagnostic charactistics compared to other materials having larger sizes. Nanoparticles also provide for more rapid dissolution of the therapeutic agent as compared to traditional formulations.

It is well known that chiral inversion of the R(−) enantiomer of ibuprofen to the S(+) form occurs readily and extensively in humans following administration. (See J. Pharmacol. 19:669–674). As a result of such bioconversion, the effective elimination half life of the S(+) enantiomer has been reported to be as much as 50% greater than that following the administration of the S(+) form alone. Unfortunately, the R(−) form of ibuprofen is characterized by a slower dissolution rate than the S(+) form in vitro thus leading one to the conclusion that the R(−) form, if administered alone, would have a substantially longer $T_{max}$ (the time to maximum absorption) consistent with a slow rate of absorption. Further, if the rate of absorption is too slow, a target analgesic level may never be reached with an equivalent dose of the faster dissolving S(+) form. Fenoprofen is also reported to have a similar rapid and complete conversion.

If rapid onset were the only criteria, then the pure S(+) form would be the most desirable. This is what is claimed in patents such as U.S. Pat. Nos. 4,851,444 and 4,877,620. However, for some multiple chronic conditions, rapid onset is less important than is the duration of the analgesic and antiinflamatory effects. Conditions where this may be important for example include rheumatoid arthritus and osteoarthritus as well as other nonspecific inflamatory or degenerative joint diseases or musculoskeletal pain or pain arising from surgical or dental procedures. Even intermediate term administration for osteopathic purposes may require long term effect. Long term effect is typically achieved with controlled release or sustained releas compositions. However, this ads complexity and complications which can increase the cost or size of the dosage form.

SUMMARY OF THE INVENTION

In accordance with the present invention there is provided a composition comprised of nanoparticles of a therapeutic agent having a surface modifier adsorbed on the surface thereof, the improvement wherein the therapeutic agent is ibuprofen or fenoprofen which is substantially enriched in the R(−) enantiomer.

By "substantially enriched" we mean that the composition contains at least about 85% of the R(−) enantiomer and preferrably about 95% or greater.

DESCRIPTION OF PREFERRED EMBODIMENTS

Figure 1:
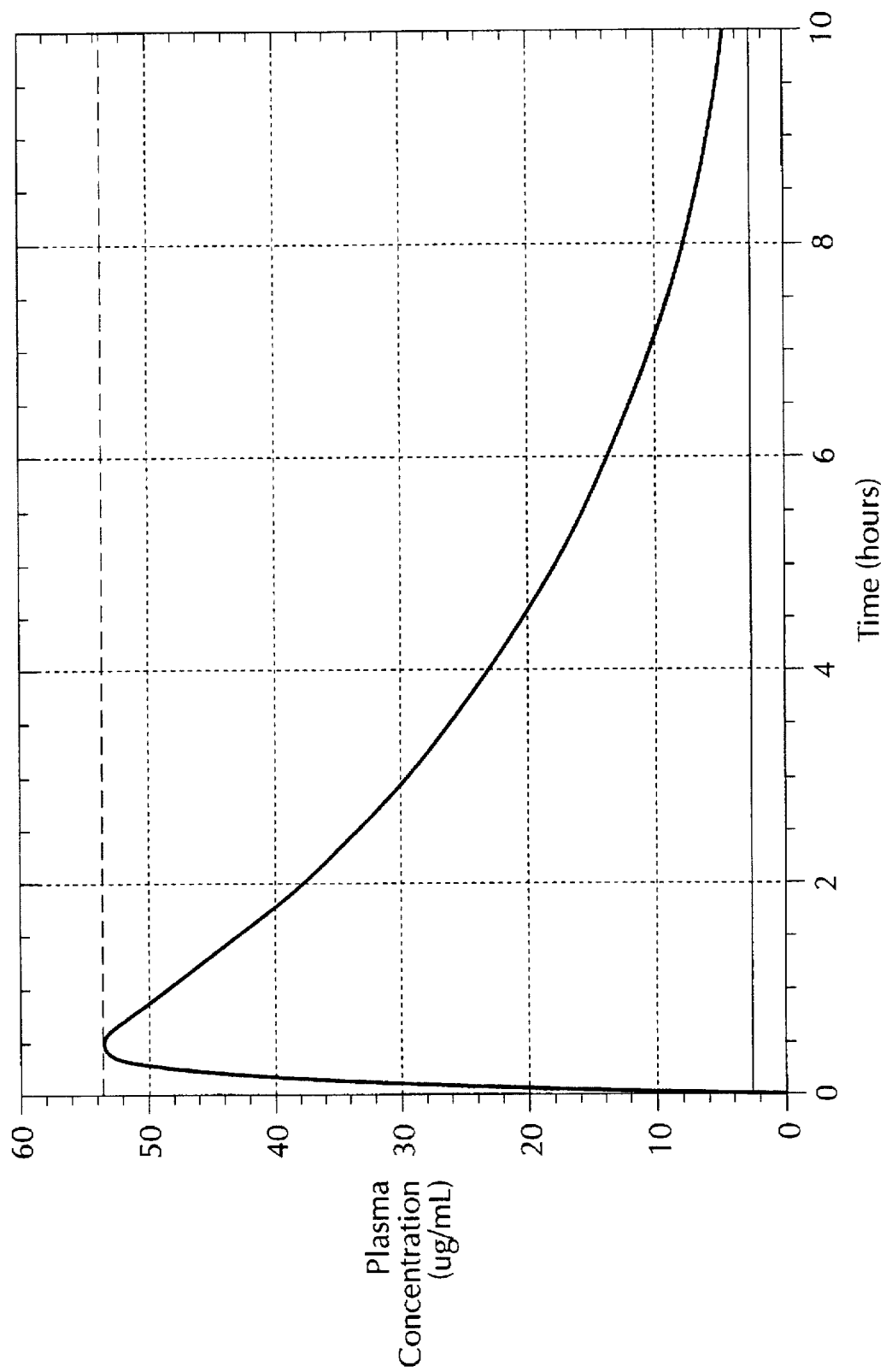
FIGS. 1 and 3 are simulated plasma concentration versus time profiles of ibuprofen administered as the R(−) form according to the invention.

Ibuprofen is commercially available under the tradenames Motrin™, Advil™ and Nuprin™ and has been extensively studied. Reference is made to the references cited in U.S. Pat. No. 4,851,444 refered to above. Ibuprofen and fenoprofen are members of a class of NSAIDS that are propionic acids derivatives Ibuprofen is a-methyl-4-(2-methyl propyl) benzene acetic acid and fenoprofen is a-methyl-3-phenoxy benzene acetic acid.

R(−) ibuprofen is commercially available from Catherx Pharmaceuticals, Jackson, Miss. The resolution of racemic mixtures can also be accomplished by methods known in the art such as described in Kaiser et al, J. Pharm Sci, Vol 65, No 2, pgs 269–273 (1976). (While this process is aimed at recovering the S(+) form, readily apparent modifications would yield the R(−) form.)

Using the nanoparticle form of R(−) ibuprofen or fenoprofen, two different effects can be balanced. With equivalent dosage intervals, the peak to trough variation will be reduced compared to administration of the S(+) form. The benefit of this is that there is better control of the analgesic or antiinflammatory effect. Alternatively, where somewhat greated peak to trough variation can be tolerated, a longer dosage interval can be used. While this might be achieved using some kind of controlled release system, such systems involve additional cost and complexity.

Surface Modifiers

The currently preferred surface modifier is hydroxypropyl methylcellulose.

Suitable surface modifiers can preferably be selected from known organic and inorganic pharmaceutical excipeints. Such excipients include various polymers, low molecular weight oligomers, natural products and surfactants. Preferred surface modifiers include nonionic and ionic surfactants.

Representative examples of surface modifiers include gelatin, casein, lecithin (phosphatides), gum acacia, cholesterol, tragacanth, stearic acid, benzalkonium chloride, calcium stearate, glycerol monostearate, cetostearyl alcohol, cetomacrogol emulsifying wax, sorbitan esters, polyotyethylene alkyl ethers, e.g., macrogol ethers such as cetomacrogol 1000, polyoxyethylene castor oil derivatives, polyoxyethylene sorbitan fatty acid esters, e.g., the commercially available Tweens™, polyethylene glycols, polyoxyethylene stearates, colloidal silicon dioxide, phosphates, sodium dodecylsulfate, carboxymethylcellulose calcium, carboxymethylcellulose sodium, methylcellulose, hydroxyethylcellulose, hydroxy propylcellulose, hydroxypropylmethylcellulose phthlate, noncrystalline cellulose, magnesium aluminum silicate, triethanolamine, polyvinyl alcohol, and polyvinylpyrrolidone (PVP). Most of these surface modifiers are known pharmaceutical excipients and are described in detail in the Handbook of Pharmaceutical Excipients, published jointly by the American Pharmaceutical Association and The Pharmaceutical Society of Great Britain, the Pharmaceutical Press,. 1986.

Particularly preferred surface modifiers include polyvinylpyrrolidone, tyloxapol, poloxamers such as Pluronic™ F68 and F108, which are block copolymers of ethylene oxide and propylene oxide, and polyxamines such as Tetronic™ 908 (also known as Poloxamine™ 908), which is a tetrafunctional block copolymer derived from sequential addition of propylene oxide and ethylene oxide to ethylenediamine, available from BASF, dextran, lecithin, dialkylesters of sodium sulfosuccinic acid, such as Aerosol OT™, which is a dioctyl ester of sodium sulfosuccinic acid, available from American Cyanimid, Duponol™ P, which is a sodium lauryl sulfate, available from DuPont, Triton™ X-200, which is an alkyl aryl polyether sulfonate, available from Rohn and Haas, Tween™ 20 and Tween™ 80, which are polyoxyethylene sorbitan fatty acid esters, available from ICI Specialty Chemicals; Carbowax™ 3550 and 934, which are polyethylene glycols available from Union Carbide; Crodesta™ F-110, which is a mixture of sucrose stearate and sucrose distearate, available from Croda Inc., Crodesta™ SL-40, which is available from Croda, Inc., and SA90HCO, which is $C_{18}H_{37}CH_2(CON(CH_3)CH_2(CHOH)_4CH_2OH)_2$. Surface modifiers which have been found to be particularly useful include Tetronic™ 908, the Tweens™, Pluronic™ F-68 and polyvinylpyrrolidone. Other useful surface modifiers include:

- decanoyl-N-methylglucamide;
- n-decyl β-D-glucopyranoside;
- n-decyl β-D-maltopyranoside;
- n-dodecyl β-D-glucopyranoside;
- n-dodecyl β-D-maltoside;
- heptanoyl-N-methylglucamide;
- n-heptyl-β-D-glucopyranoside;
- n-heptyl β-D-thioglucoside; n-hexyl β-D-glucopyranoside;
- nonanoyl-N-methylglucamide;
- n-noyl β-D-glucopyranoside;
- octanoyl-N-methylglucamide;
- n-octyl-β-D-glucopyranoside;
- octyl β-D-thioglucopyranoside; and the like.

Another useful surface modifier is tyloxapol (a nonionic liquid polymer of the alkyl aryl polyether alcohol type; also known as superinone or triton). This surface modifier is commercially available and/or can be prepared by techniques known in the art.

Another preferred surface modifier is p-isononylphenoxypoly(glycidol) also known as Olin-10G™ or Surfactant 10-G, is commercially available as 10G™ from Olin Chemicals, Stamford, Conn.

Non-Ionic Surface Modifiers

Preferred surface modifiers can be selected from known non-ionic surfactants, including the poloxamines such as Tetronic™ 908 (also known as Poloxamine™ 908), which is a tetrafunctional block copolymer derived from sequential addition of propylene oxide and ethylene oxide to ethylenediamine, available from BASF, or Tetronic™ 1508 (T-1508), or a polymer of the alkyl aryl polyether alcohol type, such as tyloxapol.

The surface modifiers are commercially available and/or can be prepared by techniques known in the art. Two or more surface modifiers can be used in combination.

Tyloxapol

Tyloxapol (4-(1,1,3,3-tetramethylbutyl)-phenol polymer with ethylene oxide and formaldehyde) is a preferred surface modifier and is a nonionic liquid polymer of the alkyl aryl polyether alcohol type. Tyloxapol, also known as "Superinone", is disclosed as useful as a nonionic surface active agent in a lung surfactant composition in U.S. Pat. No. 4,826,821 and as a stabilizing agent for 2-dimethylaminoethyl 4-n-butylaminobenzoate in U.S. Pat. No. 3,272,700.

Tyloxapol may be associated with the nanoparticles and may function as a surface modifier, as a stabilizer, and/or as a dispersant. Alternatively, the tyloxapol may serve other purposes. Tyloxapol may serve all three functions. The tyloxapol may serve as a stabilizer and/or a dispersant, whereas another compound acts as a surface modifier.

Auxiliary Surface Modifiers

Particularly preferred auxiliary surface modifiers are those which impart resistance to particle aggregation during sterilization and include dioctylsulfosuccinate (DOSS), polyethylene glycol, glycerol, sodium dodecyl sulfate, dodecyl trimethyl ammonium bromide and a charged phospholipid such as dimyristoyl phophatidyl glycerol. The surface modifiers are commercially available and/or can be prepared by techniques known in the art. Two or more surface modifiers can be used in combination.

Block Copolymer Surface Modifiers

One preferred surface modifier is a block copolymers linked to at least one anionic group. The polymers contain at least one, and preferably two, three, four or more anionic groups per molecule. Preferred anionic groups include sulfate, sulfonate, phosphonate, phosphate and carboxylate groups. The anionic groups are covalently attached to the nonionic block copolymer. The nonionic sulfated polymeric surfactant has a molecular weight of 1,000–50,000, preferably 2,000–40,000 and more preferably 3,000–30,000. In preferred embodiments, the polymer comprises at least about 50%, and more preferably, at least about 60% by weight of hydrophilic units, e.g., alkylene oxide units. The reason for this is that the presence of a major weight proportion of hydrophilic units confers aqueous solubility to the polymer.

A preferred class of block copolymers useful as surface modifiers herein includes sulfated block copolymers of ethylene oxide and propylene oxide. These block copolymers in an unsulfated form are commercially available as Pluronics™. Specific examples of the unsulfated block copolymers include F68, F108 and F127.

Another preferred class of block copolymers useful herein include tetrafunctional block copolymers derived from sequential addition of ethylene oxide and propylene oxide to ethylene diamine. These polymers, in an unsulfated form, are commercially available as Tetronics™.

Another preferred class of surface modifiers contain at least one polyethylene oxide (PEO) block as the hydrophilic portion of the molecule and at least one polybutylene oxide (PBO) block as the hydrophobic portion. Particularly preferred surface modifiers of this class are diblock, triblock, and higher block copolymers of ethylene oxide and butylene oxide, such as are represented, for example, by the following structural formula:

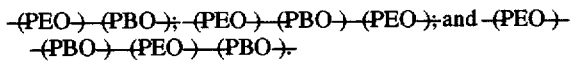

The block copolymers useful herein are known compounds and/or can be readily prepared by techniques well known in the art.

Highly preferred surface modifiers include triblock copolymers of the structure —(PEO)—(PBO)—(PEO)— having molecular weights of 3800 and 5000 which are commercially available from Dow Chemical, Midland, Mich., and are referred to as B20-3800 and B20-5000. These surface modifiers contain about 80% by weight PEO. In a preferred embodiment, the surface modifier is a triblock polymer having the structure:

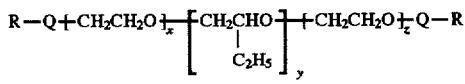

Q is an anionic group
wherein R is H or a metal cation such as Na$^+$, K$^+$ and the like, x is 15–700, y is 5–200 and z is 15–700.

Grinding

The described particles can be prepared in a method comprising the steps of dispersing the R(−) ibuprofen or fenoprofen in a liquid dispersion medium and applying mechanical means in the presence of grinding media to reduce the particle size of the therapeutic or diagnostic agent to an effective average particle size of less than about 400 nm. The particles can be reduced in size in the presence of a surface modifier. Alternatively, the particles can be contacted with a surface modifier after attrition.

The R(−) ibuprofen or fenoprofen selected is obtained commercially and/or prepared by techniques known in the art in a conventional coarse form. It is preferred, but not essential, that the particle size of the coarse R(−) ibuprofen or fenoprofen selected be less than about 100 μm as determined by sieve analysis. If the coarse particle size of the R(−) ibuprofen or fenoprofen is greater than about 100 μm, then it is preferred that the particles of the R(−) ibuprofen or fenoprofen be reduced in size to less than 100 μm using a conventional milling method such as airjet or fragmentation milling.

The coarse R(−) ibuprofen or fenoprofen selected can then be added to a liquid medium in which it is essentially insoluble to form a premix. The concentration of the R(−) ibuprofen or fenoprofen in the liquid medium can vary from about 0.1–60%, and preferably is from 5–30% (w/w). It is preferred, but not essential, that the surface modifier be present in the premix. The concentration of the surface modifier can vary from about 0.1 to about 90%, and preferably is 1–75%, more preferably 20–60%, by weight based on the total combined weight of the R(−) ibuprofen or fenoprofen and surface modifier. The apparent viscosity of the premix suspension is preferably less than about 1000 centipoise.

The premix can be used directly by subjecting it to mechanical means to reduce the average particle size in the dispersion to less than 400 nm. It is preferred that the premix be used directly when a ball mill is used for attrition. Alternatively, the R(−) ibuprofen or fenoprofen and, optionally, the surface modifier, can be dispersed in the liquid medium using suitable agitation, e.g., a roller mill or a Cowles type mixer, until a homogeneous dispersion is observed in which there are no large agglomerates visible to the naked eye. It is preferred that the premix be subjected to such a premilling dispersion step when a recirculating media mill is used for attrition.

The mechanical means applied to reduce the particle size of the R(−) ibuprofen or fenoprofen conveniently can take the form of a dispersion mill. Suitable dispersion mills include a ball mill, an attritor mill, a vibratory mill, and media mills such as a sand mill and a bead mill. A media mill is preferred due to the relatively shorter milling time required to provide the intended result, i.e., the desired reduction in particle size. For media milling, the apparent viscosity of the premix preferably is from about 100 to about 1000 centipoise. For ball milling, the apparent viscosity of the premix preferably is from about 1 up to about 100 centipoise. Such ranges tend to afford an optimal balance between efficient particle fragmentation and media erosion.

Preparation Conditions

Ibuprofen or fenoprofen should be milled under acidic conditions since under alkaline conditions, the particles will grow over time. The milling vehicle can be acidified or buffered using common pharmaceutically acceptable acids and buffers. One useful milling vehicle is dilute hydrochloric acid. The target pH should be less than the pKa of ibuprofen or fenoprofen, e.g. less than about 3.5.

The attrition time can vary widely and depends primarily upon the particular mechanical means and processing conditions selected. For ball mills, processing times of up to five days or longer may be required. On the other hand, processing times of less than 1 day (residence times of one minute up to several hours) have provided the desired results using a high shear media mill. The particles must be reduced in size at a temperature which does not significantly degrade the R(−) ibuprofen or fenoprofen. Processing temperatures of less than about 30°–40° C. are ordinarily preferred. If desired, the processing equipment can be cooled with conventional cooling equipment. The method is conveniently carried out under conditions of ambient temperature and at processing pressures which are safe and effective for the milling process. For example, ambient processing pressures are typical of ball mills, attritor mills and vibratory mills. Control of the temperature, e.g., by jacketing or immersion of the milling chamber in ice water are contemplated. Processing pressures from about 1 psi (0.07 kg/cm$^2$) up to about 50 psi (3.5 kg/cm$^2$) are contemplated. Processing pressures from about 10 psi (0.7 kg/cm$^2$) to about 20 psi (1.4 kg/cm$^2$) are typical.

The surface modifier, if it was not present in the premix, must be added to the dispersion after attrition in an amount as described for the premix above. Thereafter, the dispersion can be mixed, e.g., by shaking vigorously. Optionally, the dispersion can be subjected to a sonication step, e.g., using an ultrasonic power supply. For example, the dispersion can be subjected to ultrasonic energy having a frequency of 20–80 kHz for a time of about 1 to 120 seconds.

After attrition is completed, the grinding media is separated from the milled particulate product (in either a dry or liquid dispersion form) using conventional separation techniques, such as by filtration, sieving through a mesh screen, and the like.

Grinding Media

The grinding media for the particle size reduction step can be selected from rigid media preferably spherical or particulate in form having an average size less than about 3 mm and, more preferably, less than about 1 mm. Such media desirably can provide the particles with shorter processing times and impart less wear to the milling equipment. The selection of material for the grinding media is not believed to be critical. We have found that zirconium oxide, such as 95% $ZrO_2$ stabilized with magnesia, zirconium silicate, and glass grinding media provide particles having levels of contamination which are believed to be acceptable for the preparation of pharmaceutical compositions. However, other media, such as stainless steel, titania, alumina, and 95% $ZrO_2$ stabilized with yttrium, are expected to be useful. Preferred media have a density greater than about 3 $g/cm^3$.

Polymeric Grinding Media

The grinding media can comprise particles, preferably substantially spherical in shape, e.g., beads, consisting essentially of polymeric resin. Alternatively, the grinding media can comprise particles comprising a core having a coating of the polymeric resin adhered thereon.

In general, polymeric resins suitable for use herein are chemically and physically inert, substantially free of metals, solvent and monomers, and of sufficient hardness and friability to enable them to avoid being chipped or crushed during grinding. Suitable polymeric resins include crosslinked polystyrenes, such as polystyrene crosslinked with divinylbenzene, styrene copolymers, polycarbonates, polyacetals, such as Delrin™, vinyl chloride polymers and copolymers, polyurethanes, polyamides, poly (tetrafluoroethylenes), e.g., Teflon™, and other fluoropolymers, high density polyethylenes, polypropylenes, cellulose ethers and esters such as cellulose acetate, polyhydroxymethacrylate, polyhydroxyethyl acrylate, silicone containing polymers such as polysiloxanes and the like. The polymer can be biodegradable. Exemplary biodegradable polymers include poly(lactides), poly (glycolide) copolymers of lactides and glycolide, polyanhydrides, poly(hydroxyethyl methacylate), poly (imino carbonates), poly(N-acylhydroxyproline)esters, poly (N-palmitoyl hydroxyproline) esters, ethylene-vinyl acetate copolymers, poly(orthoesters), poly(caprolactones), and poly(phosphazenes). In the case of biodegradable polymers, contamination from the media itself advantageously can metabolize in vivo into biologically acceptable products which can be eliminated from the body.

The polymeric resin can have a density from 0.8 to 3.0 $g/cm^3$. Higher density resins are preferred inasmuch as it is believed that these provide more efficient particle size reduction.

The media can range in size from about 0.1 to 3 mm. For fine grinding, the particles preferably are from 0.2 to 2 mm, more preferably, 0.25 to 1 mm in size.

In a particularly preferred method, the R(−) ibuprofen or fenoprofen is prepared in the form of submicron particles by pre-grinding the agent in the presence of a grinding media having a mean particle size of less than about 75 microns.

The core material of the grinding media preferably can be selected from materials known to be useful as grinding media when fabricated as spheres or particles. Suitable core materials include zirconium oxides (such as 95% zirconium oxide stabilized with magnesia or yttrium), zirconium silicate, glass, stainless steel, titania, alumina, ferrite and the like. Preferred core materials have a density greater than about 2.5 $g/cm^3$. The selection of high density core materials is believed to facilitate efficient particle size reduction.

Useful thicknesses of the polymer coating on the core are believed to range from about 1 to about 500 microns, although other thicknesses outside this range may be useful in some applications. The thickness of the polymer coating preferably is less than the diameter of the core.

The cores can be coated with the polymeric resin by techniques known in the art. Suitable techniques include spray coating, fluidized bed coating, and melt coating. Adhesion promoting or tie layers can optionally be provided to improve the adhesion between the core material and the resin coating. The adhesion of the polymer coating to the core material can be enhanced by treating the core material to adhesion promoting procedures, such as roughening of the core surface, corona discharge treatment, and the like.

Continuous Grinding

In a preferred grinding process, the particles are made continuously rather than in a batch mode. The continuous method comprises the steps of continuously introducing the R(−) ibuprofen or fenoprofen and rigid grinding media into a milling chamber, contacting the ibuprofen or fenoprofen with the grinding media while in the chamber to reduce the particle size of the agent, continuously removing the ibuprofen or fenoprofen and the grinding media from the milling chamber, and thereafter separating the ibuprofen or fenoprofen from the grinding media.

The R(−) ibuprofen or fenoprofen and the grinding media are continuously removed from the milling chamber. Thereafter, the grinding media is separated from the milled particulate ibuprofen or fenoprofen (in either a dry or liquid dispersion form) using conventional separation techniques, in a secondary process such as by simple filtration, sieving through a mesh filter or screen, and the like. Other separation techniques such as centrifugation may also be employed.

In a preferred embodiment, the ibuprofen or fenoprofen and grinding media are recirculated through the milling chamber. Examples of suitable means to effect such recirculation include conventional pumps such as peristaltic pumps, diaphragm pumps, piston pumps, centrifugal pumps and other positive displacement pumps which do not use sufficiently close tolerances to damage the grinding media. Peristaltic pumps are generally preferred.

Another variation of the continuous process includes the use of mixed media sizes. For example, larger media may be employed in a conventional manner where such media is restricted to the milling chamber. Smaller grinding media may be continuously recirculated through the system and permitted to pass through the agitated bed of larger grinding media. In this embodiment, the smaller media is preferably between about 1 and 300 mm in mean particle size and the larger grinding media is between about 300 and 1000 mm in mean particle size.

Precipitation Method

Another method of forming the desired nanoparticle dispersion is by microprecipitation. This is a method of preparing stable dispersions of R(−) ibuprofen or fenoprofen in the presence of a surface modifying and colloid stability enhancing surface active agent free of trace of any toxic solvents or solubilized heavy metal inpurities by the following procedural steps:

1. Dissolving the R(−) ibuprofen or fenoprofen in aqueous base with stirring,
2. Adding above #1 formulation with stirring to a surface active surfactant (or surface modifiers) solution to form a clear solution, and,
3. Neutralizing above formulation #2 with stirring with an appropriate acid solution. The procedure can be followed by:

4. Removal of formed salt by dialysis or diafiltration and
5. Concentration of dispersion by conventional means.

This microprecipitation process produces dispersion of R(−) ibuprofen or fenoprofen with Z-average particle diameter less than 400 nm (as measured by photon correlation spectroscopy) that are stable in particle size upon keeping under room temperature or refrigerated conditions. Such dispersions also demonstrate limited particle size growth upon autoclave-decontamination conditions used for standard blood-pool pharmaceutical agents.

Step 3 can be carried out in semicontinuous, continuous batch, or continuous methods at constant flow rates of the reacting components in computer-controlled reactors or in tubular reactors where reaction pH can be kept constant using pH-stat systems. Advantages of such modifications are that they provide cheaper manufacturing procedures for large-scale production of nanoparticulate dispersion systems.

Additional surface modifier may be added to the dispersion after precipitation. Thereafter, the dispersion can be mixed, e.g., by shaking vigorously. Optionally, the dispersion can be subjected to a sonication step, e.g., using an ultrasonic power supply. For example, the dispersion can be subjected to ultrasonic energy having a frequency of 20–80 kHz for a time of about 1 to 120 seconds.

In a preferred embodiment, the above procedure is followed with step 4 which comprises removing the formed salts by diafiltration or dialysis. This is done in the case of dialysis by standard dialysis equipment and by diafiltration using standard diafiltration equipment known in the art. Preferably, the final step is concentration to a desired concentration of the agent dispersion. This is done either by diafiltration or evaporation using standard equipment known in this art.

An advantage of microprecipitation is that unlike milled dispersion, the final product is free of heavy metal contaminants arising from the milling media that must be removed due to their toxicity before product is formulated.

A further advantage of the microprecipitation method is that unlike solvent precipitation, the final product is free of any trace of trace solvents that may be toxic and must be removed by expensive treatments prior to final product formulation.

In another preferred embodiment of the microprecipitation process, a crystal growth modifier is used. A crystal growth modifier is defined as a compound that in the co-precipitation process incorporates into the crystal structure of the microprecipitated crystals of the pharmaceutical agent, thereby hindering growth or enlargement of the microcrystalline precipitate, by the so called Ostwald ripening process. A crystal growth modifier (or a CGM) is a chemical that is at least 75% identical in chemical structure to the pharmaceuticl agent. By "identical" is meant that the structures are identical atom for atom and their connectivity. Structural identity is charactarized as having 75% of the chemical structure, on a molecular weight basis, identical to the therapeutic or diagnostic agent. The remaining 25% of the structure may be absent or replaced by different chemical structure in the CGM. The crystal growth modifier is dissolved in step #1 with the therapeutic or diagnostic agent.

Particle Size

AS used herein, particle size refers to a number average particle size as measured by conventional particle size measuring techniques well known to those skilled in the art, such as sedimentation field flow fractionation, photon correlation spectroscopy, or disk centrifugation. When photon correlation spectroscopy (PCS) is used as the method of particle sizing the average particle diameter is the Z-average particle diameter known to those skilled in the art. By "an effective average particle size of less than about 400 nm" it is meant that at least 90% of the particles have a weight average particle size of less than about 400 nm when measured by the above-noted techniques. In preferred embodiments, the effective average particle size is less than about 300 nm and more preferrably less than about 250 nm. In some embodiments, an effective average particle size of less than about 100 nm has been achieved. With reference to the effective average particle size, it is preferred that at least 95% and, more preferably, at least 99% of the particles have a particle size less than the effective average, e.g., 400 nm. In particularly preferred embodiments, essentially all of the particles have a size less than 400 nm. In some embodiments, essentially all of the particles have a size less than 250 nm.

Dosage Forms

The resulting dispersion is stable and consists of the liquid dispersion medium and the described particles. The dispersion of surface modified R(−) ibuprofen or fenoprofen containing nanoparticles can be spray coated onto sugar spheres or onto a pharmaceutical excipient in a fluid-bed spray coater by techniques well known in the art.

Solid Forms

Solid dosage forms for oral administration include capsules, tablets, pills, powders and granules. In such solid dosage forms, the active compound is admixed with at least one inert customary excipient (or carrier) such as sodium citrate or dicalcium phosphate or (a) fillers or extenders, as for example, starches, lactose, sucrose, glucose, mannitol and silicic acid, (b) binders, as for example, carboxymethylcellulose, alignates, gelatin, polyvinylpyrrolidone, sucrose and acacia, (c) humectants, as for example, glycerol, (d) disintegrating agents, as for example, agar-agar, calcium carbonate, potato or tapioca starch, alginic acid, certain complex silicates and sodium carbonate, (e) solution retarders, as for example paraffin, (f) absorption accelerators, as for example, quaternary ammonium compounds, (g) wetting agents, as for example, cetyl alcohol and glycerol monostearate, (h) adsorbents, as for example, kaolin and bentonite, and (i) lubricants, as for example, talc, calcium stearate, magnesium stearate, solid polyethylene glycols, sodium lauryl sulfate or mixtures thereof. In the case of capsules, tablets and pills, the dosage forms may also comprise buffering agents.

Solid compositions of a similar type may also be employed as fillers in soft and hard-filled gelatin capsules using such excipients as lactose or milk sugar as well as high molecular weight polyethyleneglycols, and the like.

Solid dosage forms such as tablets, dragees, capsules, pills and granules can be prepared with coatings and shells, such as enteric coatings and others well known in the art. They may contain opacifying agents, and can also be of such composition that they release the active compound or compounds in a certain part of the intestinal tract in a delayed manner. Examples of embedding compositions which can be used are polymeric substances and waxes.

The active compounds can also be in micro-encapsulated form, if appropriate, with one or more of the above-mentioned excipients.

Liquid Forms

Liquid dosage forms for oral administration include pharmaceutically acceptable emulsions, solutions, suspensions, syrups and elixirs. In addition to the active compounds, the liquid dosage forms may contain inert diluents commonly used in the art, such as water or other solvents, solubilizing agents and emulsifiers, as for example, ethyl alcohol, isopropyl alcohol, ethyl carbonate, ethyl acetate, benzyl alcohol, benzyl benzoate, propyleneglycol, 1,3-butyleneglycol, dimethylformamide, oils, in particular, cottonseed oil, groundnut oil, corn germ oil, olive oil, castor oil and sesame oil, glycerol, tetrahydrofurfuryl alcohol, polyethyleneglycols and fatty acid esters of sorbitan or mixtures of these substances, and the like.

Dosage Levels

Actual dosage levels of active ingredients in the compositions may be varied so as to obtain an amount of active ingredient that is effective to obtain a desired therapeutic or diagnostic response for a particular composition and method of administration. The selected dosage level therefore depends upon the desired therapeutic or diagnostic effect, on the route of administration, on the desired duration of treatment and other factors.

The total daily dose administered to a host in single or divided dose may be in amounts, for example, of from about 1 nanomol to about 5 micromoles per kilogram of body weight. Dosage unit compositions may contain such amounts of such submultiples thereof as may be used to make up the daily dose. It will be understood, however, that the specific dose level for any particular patient will depend upon a variety of factors including the body weight, general health, sex, diet, time and route of administration, rates of absorption and excretion, combination with other therapeutic agents and the severity of the particular disease being treated.

Ratios

The relative amount of R(−) ibuprofen or fenoprofen and surface modifier can vary widely and the optimal amount of the surface modifier can depend, for example, upon the particular R(−) ibuprofen or fenoprofen and surface modifier selected, the critical micelle concentration of the surface modifier if it forms micelles, the hydrophilic lipophilic balance (HLB) of the stabilizer, the melting point of the stabilizer, its water solubility, the surface tension of water solutions of the stabilizer, etc. The surface modifier preferably is present in an amount of about 0.1–10 mg per square meter surface area of the therapeutic or diagnostic agent. The surface modifier can be present in an amount of 0.1–90%, preferably 20–60% by weight based on the total weight of the dry particle.

Additives

Besides such inert diluents, the composition can also include adjuvants, such as wetting agents, emulsifying and suspending agents, sweetening, flavoring and perfuming agents.

Suspensions, in addition to the active compounds, may contain suspending agents, as for example, ethoxylated isostearyl alcohols, polyoxyethylene sorbitol and sorbitan esters, microcrystalline cellulose, aluminum metahydroxide, bentonite, agar-agar and tragacanth, or mixtures of these substances, and the like.

These compositions may also contain adjuvants such as preserving, wetting, emulsifying, and dispensing agents.

Prevention of the action of microorganisms can be ensured by various antibacterial and antifungal agents, for example, parabens, chlorobutanol, phenol, sorbic acid, and the like. It may also be desirable to include isotonic agents, for example sugars, sodium chloride and the like. Prolonged absorption of the injectable pharmaceutical form can be brought about by the use of agents delaying absorption, for example, aluminum monostearate and gelatin.

Method of Treating

A method of treating or diagnosing a mammal comprises the step of administering to the mammal in need of treatment an effective amount of the above-described R(−) ibuprofen or fenoprofen composition. The selected dosage level of the R(−) ibuprofen or fenoprofen for treatment is effective to obtain a desired therapeutic response for a particular composition and method of administration.

Examples

Simulated pharmacokinetic profiles were generated using *Scientist* software available from MicroMath Scientific Software Inc., Salt Lake City Utah. This software includes a library of pharmacokinetic models that can be manipulated based on specific parameters that the operator selects. For the sumulations presentd here, a one compartment (biexponential) model with first order input and first order elimination was employed. Values of absorption (Ka) and elimination (Ke) rate constants as well as fraction abosorbed (Fd) and volume of distribution were obtained from the literature for ibuprofen.

Figure 2:
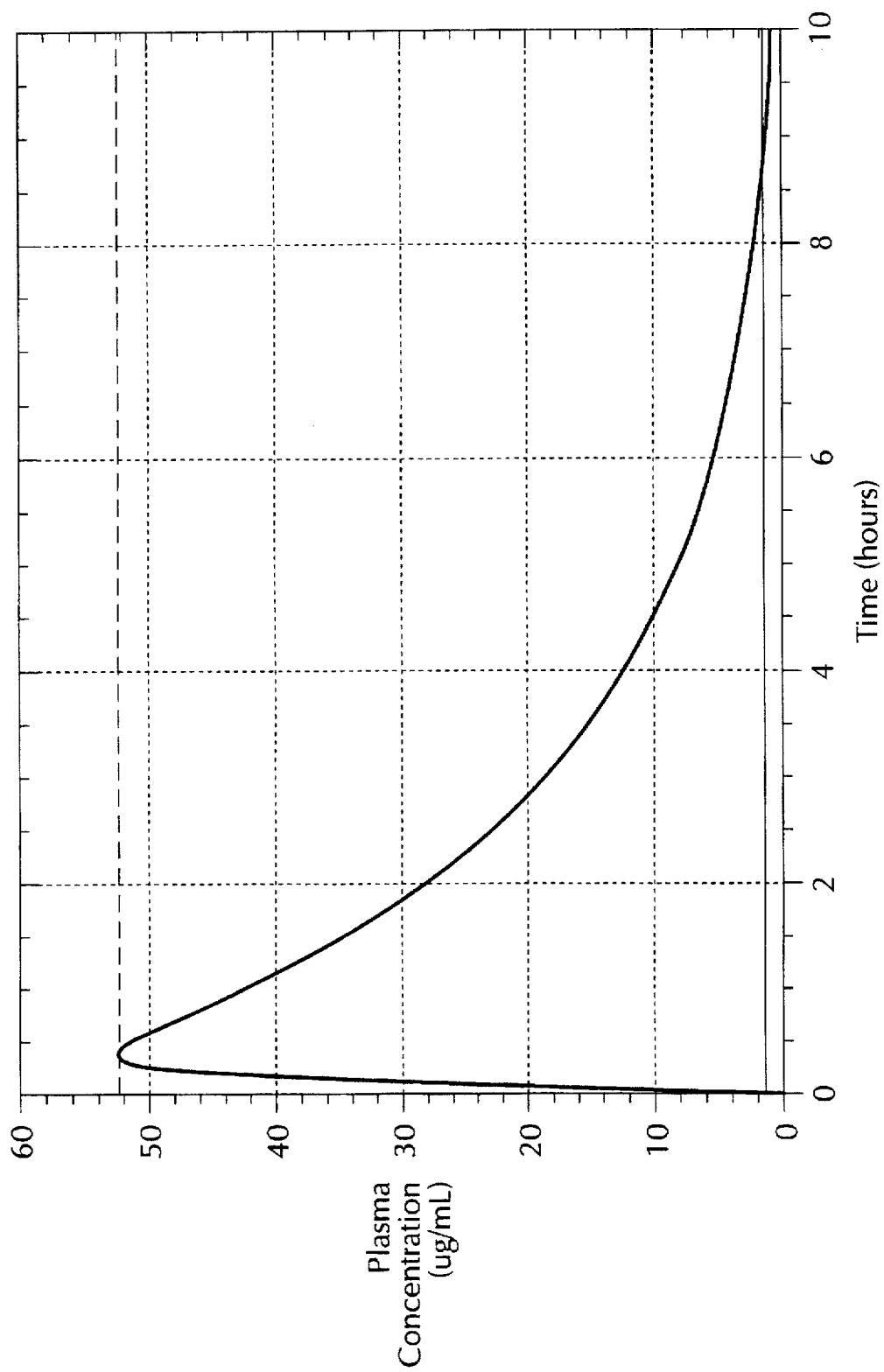
FIGS. 2 and 4 are simulated plasma concentration versus time profiles of ibuprofen administered as the S(+) form as a comparison.
Figure 3:
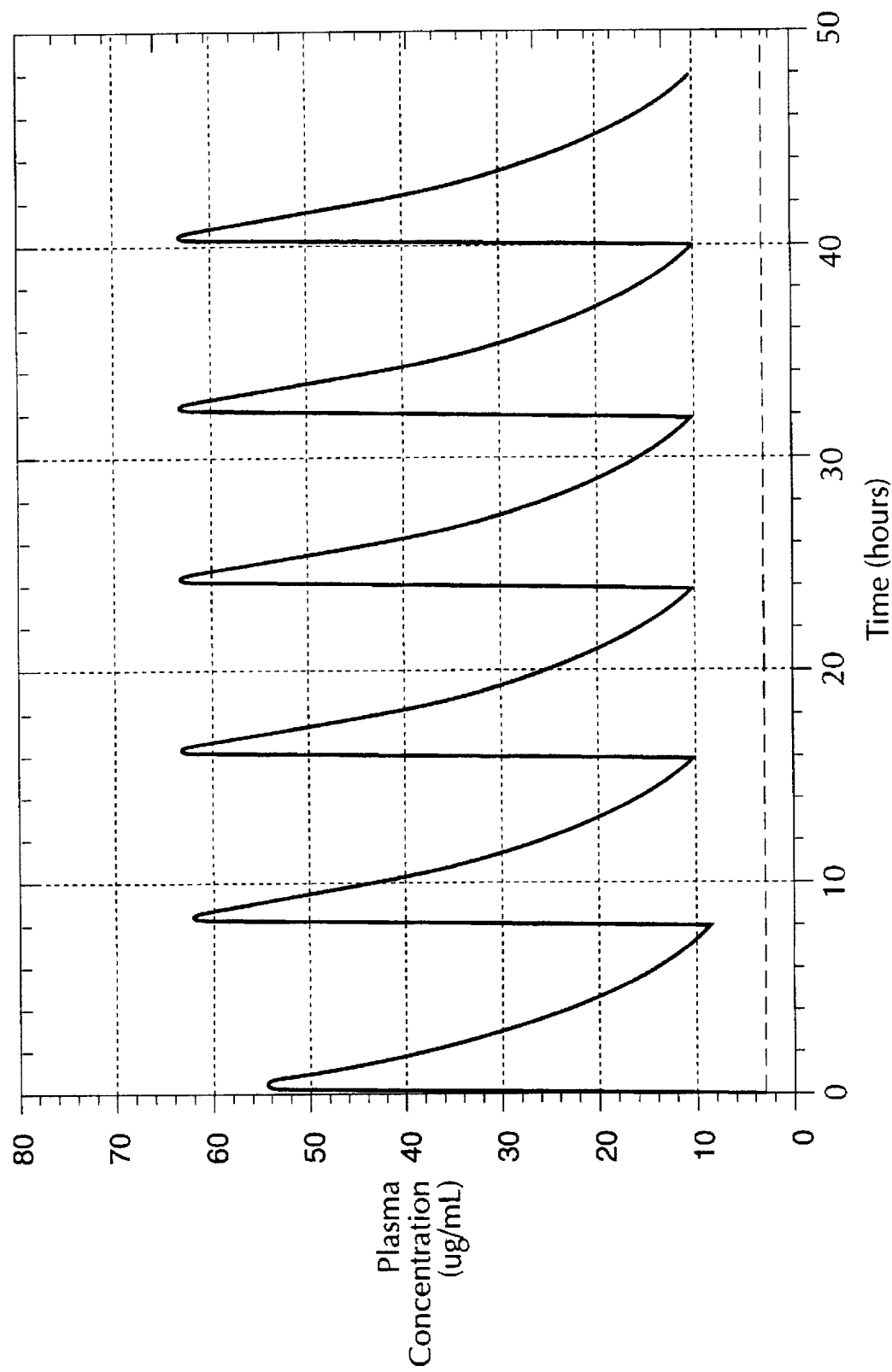
Figure 4:
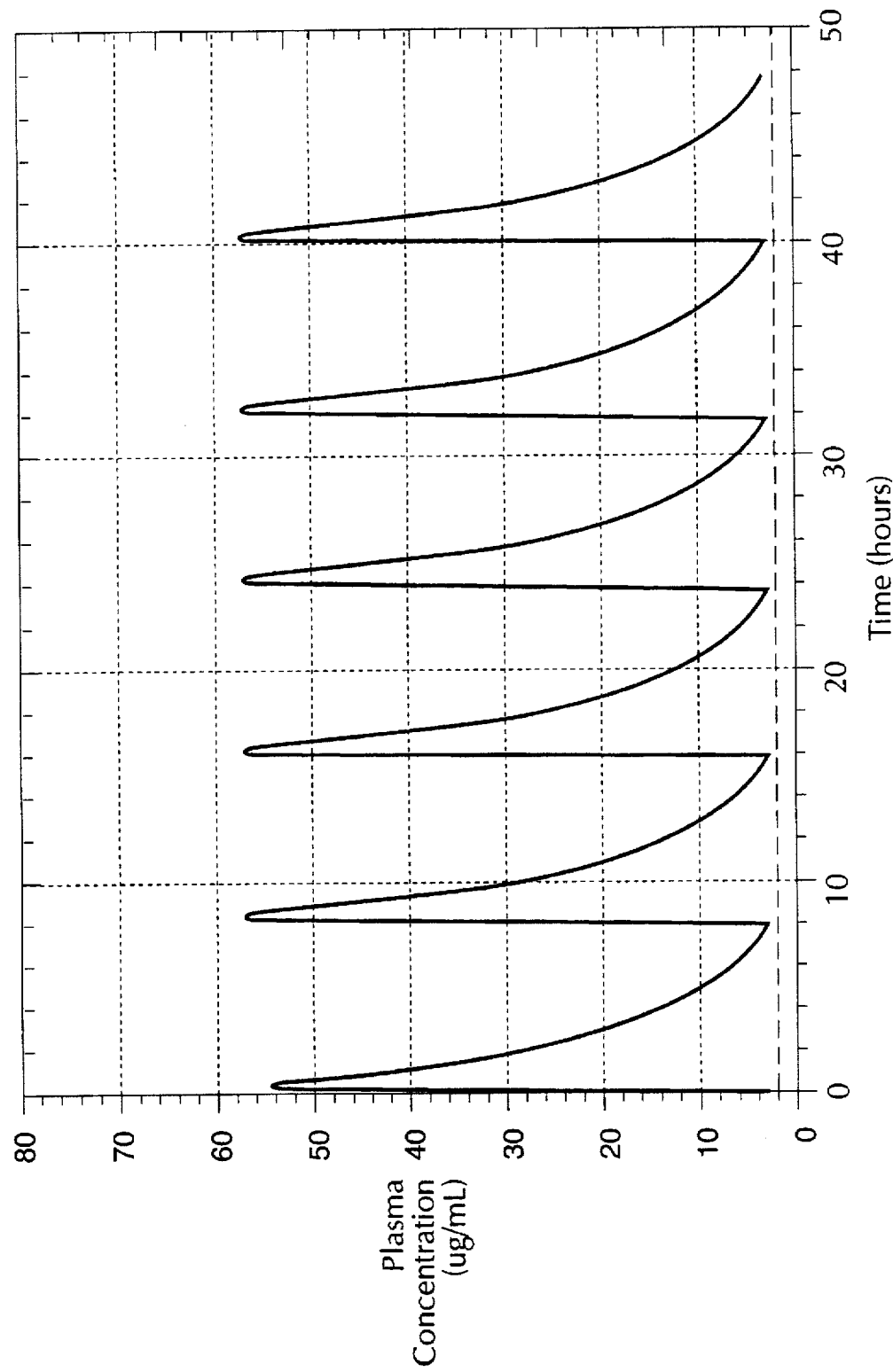

FIGS. 1 and 2 (FIG. 1 illustrating the invention and FIG. 2 illustrating S(+) administration) represent plasma concentration vs. time profiles following a single 600 mg dose. FIGS. 3 and 4 (FIG. 3 illustrating the invention and FIG. 4 illustrating S(+) administration) represents the arrival of steady state conditions following multiple 600 mg doses at 8 hour intervals.

The invention has been described with particular reference to preferred embodiments thereof, but it will be understood that variations and modifications can be effected within the spirit and scope of the invention.

We claim:

1. A composition comprised of nanoparticles of a therapeutic agent, the nanoparticles having a surface modifier adsorbed on the surface thereof, wherein the surface modifier is present in an amount of 0.1 to 90% by weight of the total weight of the surface modifier and therapeutic agent, the nanoparticles have an effective particle size of less than about 400 nm, and the therapeutic agent is ibuprofen or fenoprofen of which at least about 95% is the R (−) enantiomer.

2. The composition of claim 1 wherein the surface modifier is hydroxypropyl methylcellulose.

3. A longer acting dosage form of ibuprofen or fenoprofen, the dosage form consisting essentially of nanoparticles of ibuprofen or fenoprofen, of which at least about 95% is the R(−) enantiomer, the nanoparticles having a surface modifier adsorbed on the surface thereof, wherein the surface modifier is present in an amount of 0.1 to 90% by weight of the total weight of the surface modifier and the ibuprofen or fenoprofen and the nanoparticles have an effective particle size of less than about 400 nm.

* * * * *